(12) United States Patent
Meier et al.

(10) Patent No.: US 12,005,064 B2
(45) Date of Patent: Jun. 11, 2024

(54) PHARMACEUTICAL COMPOSITION COMPRISING NON-IONIC SURFACTANTS

(71) Applicants: Hoffmann-La Roche Inc., Little Falls, NJ (US); Chugai Seiyaku Kabushiki Kaisha, Tokyo (JP)

(72) Inventors: Susanne Meier, Dussnang (CH); Carsten Bruesewitz, Eptingen (CH)

(73) Assignees: Hoffmann-La Roche Inc., Little Falls, NJ (US); Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 16/773,734

(22) Filed: Jan. 27, 2020

(65) Prior Publication Data

US 2020/0397794 A1 Dec. 24, 2020

Related U.S. Application Data

(63) Continuation of application No. 15/383,164, filed on Dec. 19, 2016, now abandoned, which is a continuation of application No. PCT/EP2015/063469, filed on Jun. 16, 2015.

(30) Foreign Application Priority Data

Jun. 18, 2014 (EP) .................................... 14173023
Jun. 27, 2014 (EP) .................................... 14174664

(51) Int. Cl.
| | | |
|---|---|---|
| A61K 31/5377 | (2006.01) | |
| A61K 9/48 | (2006.01) | |
| A61K 47/14 | (2017.01) | |
| A61K 47/22 | (2006.01) | |
| A61K 47/26 | (2006.01) | |

(52) U.S. Cl.
CPC ........ *A61K 31/5377* (2013.01); *A61K 9/4858* (2013.01); *A61K 47/14* (2013.01); *A61K 47/22* (2013.01); *A61K 47/26* (2013.01)

(58) Field of Classification Search
None
See application file for complete search history.

(56) References Cited

U.S. PATENT DOCUMENTS

| | | | |
|---|---|---|---|
| 3,881,012 A | 4/1975 | Mima et al. | |
| 9,078,921 B2 | 7/2015 | Rosenberg et al. | |
| 9,126,931 B2 ‡ | 9/2015 | Kinoshita | ............ C07D 209/56 |
| 9,365,514 B2 | 6/2016 | Furumoto et al. | |
| 9,444,922 B2 | 9/2016 | Kinoshita et al. | |
| 9,642,796 B2 | 5/2017 | Packhaeuser et al. | |
| 9,714,229 B2 | 7/2017 | Tanaka et al. | |
| 10,344,014 B2 | 7/2019 | Shiraki et al. | |
| 10,646,468 B2 | 5/2020 | Furumoto et al. | |
| 10,668,075 B2 | 6/2020 | Kodama et al. | |
| 10,774,067 B2 | 9/2020 | Shiraki et al. | |
| 11,077,093 B2 | 8/2021 | Sakamoto et al. | |
| 2009/0263479 A1 | 10/2009 | Packhaeuser et al. | |
| 2010/0247635 A1 ‡ | 9/2010 | Rosenberg | ............. A61K 9/145 424/455 |
| 2010/0310648 A1 ‡ | 12/2010 | Packhaeuser | ........ A61K 9/0053 424/451 |
| 2012/0083488 A1 ‡ | 4/2012 | Kinoshita | ............ C07D 209/56 514/217.03 |
| 2016/0304308 A1 | 10/2016 | Kinoshita | |
| 2020/0017442 A1 | 1/2020 | Kinoshita et al. | |
| 2020/0246349 A1 | 8/2020 | Kodama | |
| 2021/0052550 A1 | 2/2021 | Furumoto et al. | |
| 2021/0238160 A1 | 8/2021 | Shiraki et al. | |
| 2021/0322380 A1 | 10/2021 | Sakamoto et al. | |

FOREIGN PATENT DOCUMENTS

| | | |
|---|---|---|
| CN | 101138550 | 12/2008 |
| JP | 2006-518353 | 8/2006 |
| JP | 2009-543849 | 12/2009 |
| JP | 2010-527925 | 8/2010 |
| JP | 2012-529490 | 11/2012 |
| WO | 03/032949 A1 | 4/2003 |
| WO | 2004/073592 | 9/2004 |
| WO | 2008/009689 A1 | 1/2008 |
| WO | 2008/078922 | 7/2008 |
| WO | 2008/091855 A1 | 7/2008 |
| WO | 2008/143960 | 11/2008 |
| WO | 2009/071326 A2 | 6/2009 |
| WO | 2009/130204 | 10/2009 |
| WO | 2010/143074 A2 | 12/2010 |
| WO | 2011/112558 A2 | 9/2011 |
| WO | 2011/117711 A1 | 9/2011 |
| WO | 2012/001403 A1 | 1/2012 |
| WO | 2012/023597 A1 | 2/2012 |

(Continued)

OTHER PUBLICATIONS

International Search Report issued in International Application No. PCT/EP2015/063469, dated Aug. 12, 2015, in 4 pages.
V. I. Chueshov, "A process for manufacturing medicines: the manual" Kharkov (Kharkov, NFAU (machine translation)), 2:353-355 ( 2002).
Written Opinion of International Searching Authority issued in International Application No. PCT/EP2015/063469, dated Aug. 12, 2015, in 8 pages.
(Chemical Properties of Vitamin E TPGS, Antares Health Products, retrieved from the internet <https://www.tpgs.com/tpgs-technical-info/tpgs-properties>, Published 2022, Printed Jun. 22, 2022. 2 Pages).

(Continued)

*Primary Examiner* — Abigail VanHorn
*Assistant Examiner* — Ali S Saeed
(74) *Attorney, Agent, or Firm* — Nicole M. Fortuné

(57) ABSTRACT

The present invention relates to a pharmaceutical composition comprising poorly soluble compounds such as BSC class II or IV kinase inhibitors, a process for the preparation thereof and its use in the treatment of diseases, in particular cancer, further particularly in non-small lung cancer.

41 Claims, 3 Drawing Sheets

(56) References Cited

FOREIGN PATENT DOCUMENTS

WO 2012/138783 A2 10/2012

OTHER PUBLICATIONS (Propylene Glycol Monolaurate, Chemical Trading Guide Encyclopedia, Published 2010, printed 2022, retrieved from the internet <https://www.guidechem.com/encyclopedia/propylene-glycol-monolaurate-dic372770.html>, 2 Pages).
(Wikipedia, Polysorbate 20, retrieved from the internet <https://en.wilcipedia.org/wiki/Polysorbate_20>, Published Mar. 8, 2022, Printed Jun. 22, 2022, 1 Page).
(Wikipedia, Polysorbate 80, retrieved from the internet <https://en.wikipedia.org/wiki/Polysorbate_80>, Published Mar. 23, 2022, Printed Jun. 22, 2022, 1 Page).
(Wikipedia, Sorbitan Monolaurate, accessed from the Internet <https://en.wikipedia.org/wiki/Sorbitan_monolaurate>, Last Edited Feb. 28, 2021, Printed Jun. 22, 2022, 1 Page).
Griffin, "Calculation of HLB Values of Non-Ionic Surfactants" J Soc Cosmet Chem 5:249-256 (1954).
Griffin, W., et al., "Classification of Surface-Active Agents by 'HLB'" J Soc Cosmet Chem 1:311-326 (1949).

‡ imported from a related application

PHARMACEUTICAL COMPOSITION COMPRISING NON-IONIC SURFACTANTS

CROSS REFERENCE TO RELATED APPLICATIONS

This application is a continuation of U.S. application Ser. No. 15/383,164, filed Dec. 19, 2016, which is a continuation of International Application No. PCT/EP2015/063469, file Jun. 16, 2015, claiming priority to Foreign Application No. EP 14173023.4, filed Jun. 18, 2014 and Foreign Application No. EP 14174664.4, filed Jun. 27, 2014, which are/is incorporated herein by reference in its entirety.

The present invention relates to a pharmaceutical composition, particularly comprising 9-ethyl-6,6-dimethyl-8-(4-morpholin-4-yl-piperidin-1-yl)-11-oxo-6,11-dihydro-5H-benzo[b]carbazole-3-carbonitrile or pharmaceutically acceptable salt thereof, further particularly comprising 9-ethyl-6,6-dimethyl-8-(4-morpholin-4-yl-piperidin-1-yl)-11-oxo-6,11-dihydro-5H-benzo[b]carbazole-3-carbonitrile hydrochloride, a process for the preparation thereof and its use in the treatment of diseases, in particular cancer, further particularly in non-small lung cancer.

9-ethyl-6,6-dimethyl-8-(4-morpholin-4-yl-piperidin-1-yl)-11-oxo-6,11-dihydro-5H-benzo[b]carbazole-3-carbonitrile is a tetracyclic compounds known to have an Anaplastic Lymphoma Kinase (ALK) inhibitory activity (WO2010/143664).

Anaplastic Lymphoma Kinase (ALK) is one of the receptor type tyrosine kinases belonging to an insulin receptor family. It is reported that gene alteration of ALK causes production of abnormal kinase fused with other gene.

Examples of the disorders accompanied with ALK abnormality include cancer and cancer metastasis. Thus, an inhibitor for ALK will provide pharmaceuticals that are effective for treatment and prevention of the disorders.

Such pharmaceuticals are required to be developed in the form of orally administrable formulation. However, the properties of an orally administrable formulation depend on the level of bioavailability of a pharmaceutical compound. As a factor which affects bioavailability, water solubility and solubilisation speed of a pharmaceutical compound can be considered. In general, when a compound which is poorly water-soluble or insoluble in water is orally administered, it shows poor bioavailability. A slow solubilisation also leads to poor bioavailability, if the solubilisation time exceeds the transit time in the absorptive regions of the gastrointestinal tract. Increasing the bioavailability by improving an oral absorption property of an active ingredient is also important in terms of obtaining stable and reproducible exhibition of pharmaceutical effect of the active ingredient.

Although 9-ethyl-6,6-dimethyl-8-(4-morpholin-4-yl-piperidin-1-yl)-11-oxo-6,11-dihydro-5H-benzo[b]carbazole-3-carbonitrile used in the present invention has an excellent ALK inhibitory activity, it is also a weak base that is practically insoluble in water across the whole pH range. It is also poorly soluble in a diverse set of excipients, covering an HLB range of 1 to 20 and above. Due to its poorly water-soluble or insoluble property in water, further studies have been needed to develop them in the form of orally administrable formulation.

The present invention provides a pharmaceutical composition that may increase bioavailability of 9-ethyl-6,6-dimethyl-8-(4-morpholin-4-yl-piperidin-1-yl)-11-oxo-6,11-dihydro-5H-benzo[b]carbazole-3-carbonitrile for the treatment of cancer in human. Furthermore, the drug is administered in a dispersed form which facilitates rapid and complete dispersion of the compound upon contact with enteric or gastrointestinal body fluids. A complete and fine dispersion of the drug in turn enables a quick solubilisation of the compound. By this, the pharmaceutical compositions in this invention may also decrease the intra- and interindividual variability in human exposure that is often experienced with poorly bioavailable drugs. It also avoids any barriers due to solubility, such as the use of high amount of excipient usually used to solubilized or dispersed in solution poorly soluble compounds.

Figure 1:
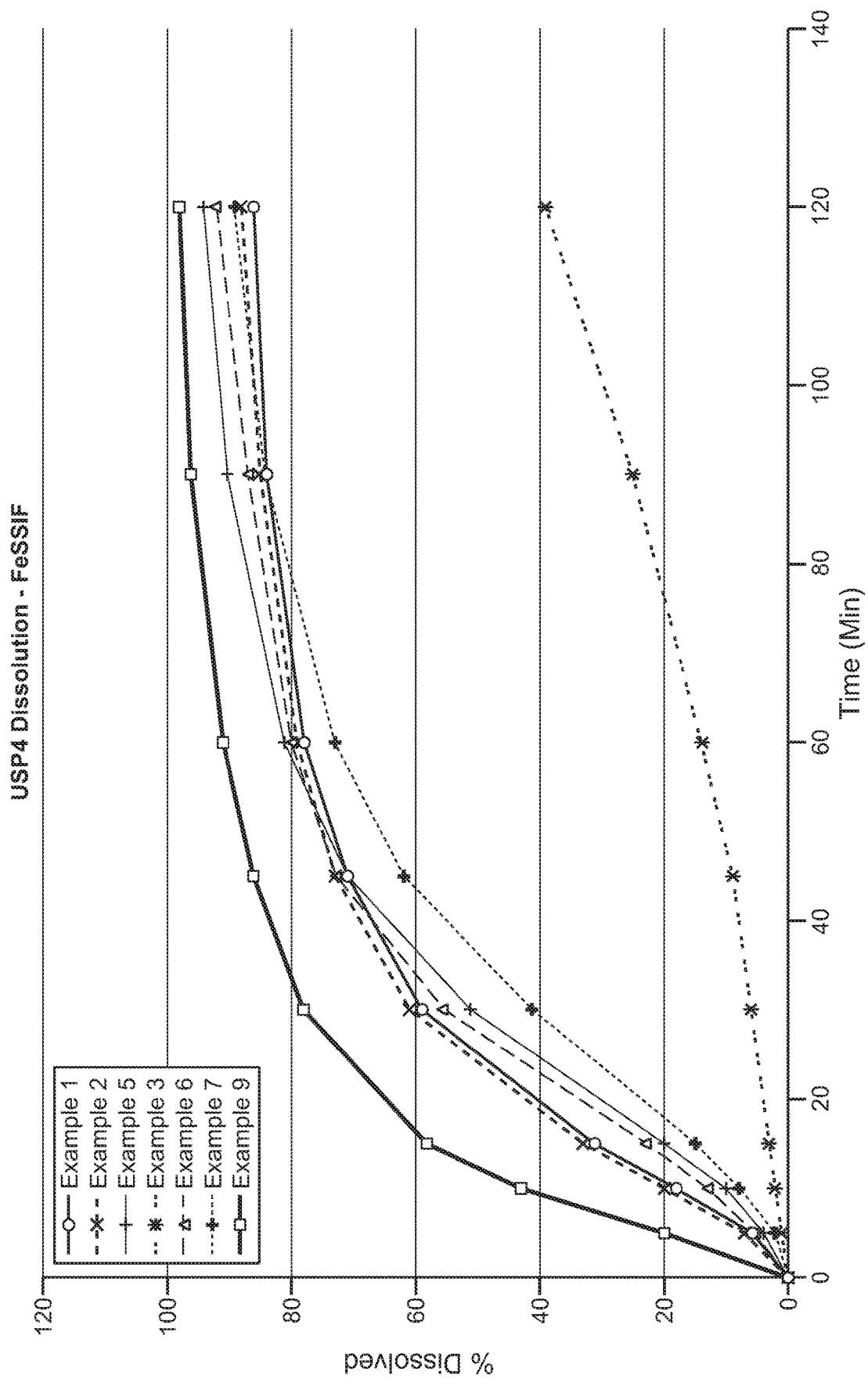
FIG. 1 illustrates the dissolution results in biorelevant media (FeSSIF/USP4) of capsules produced according to examples 1, 2, 3, 5, 6, 7 and 9.
Figure 2:
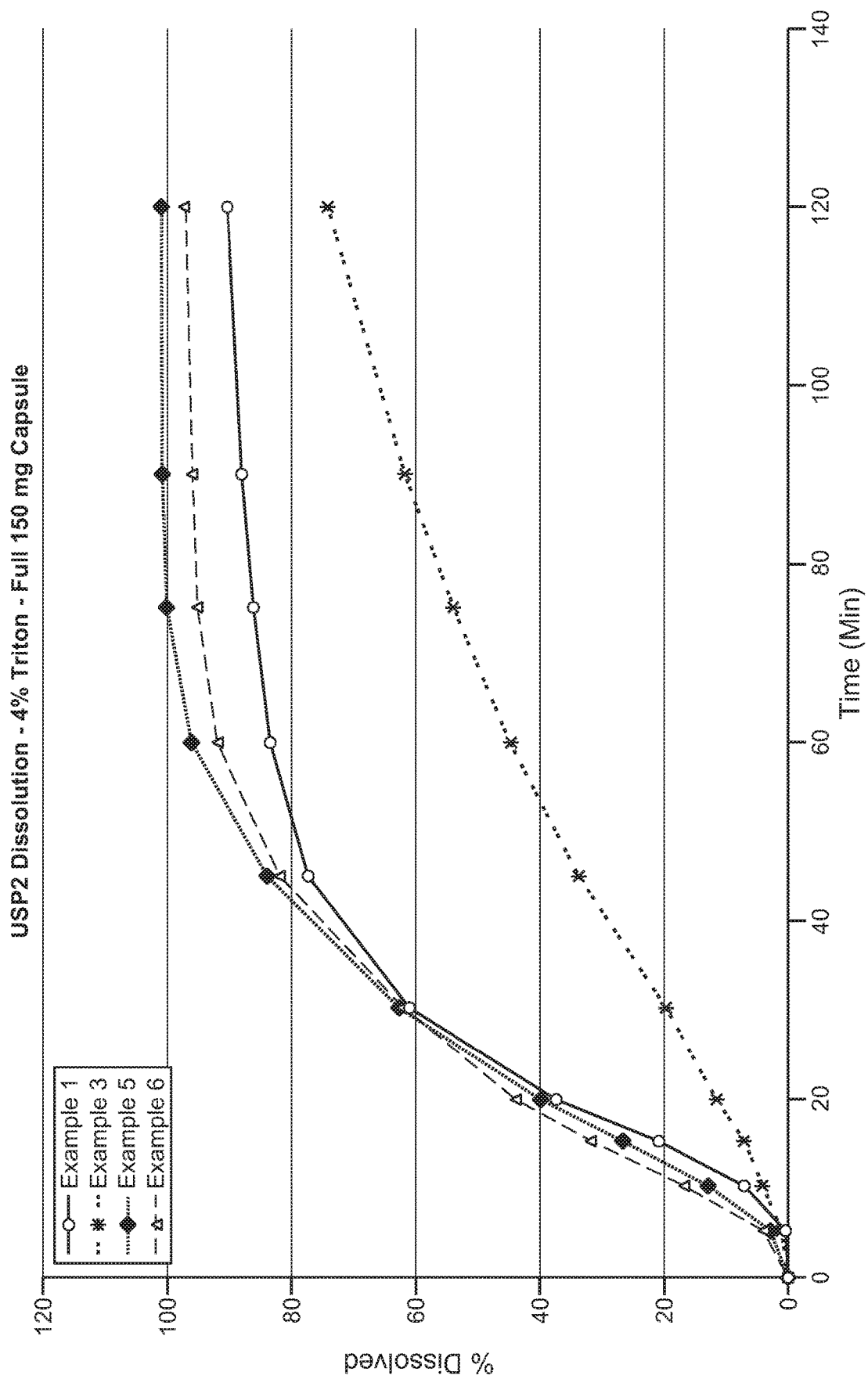
FIG. 2 illustrates the dissolution results in Triton media (4% Triton/USP2) of capsules produced according to examples 1, 3, 5 and 6.
Figure 3:
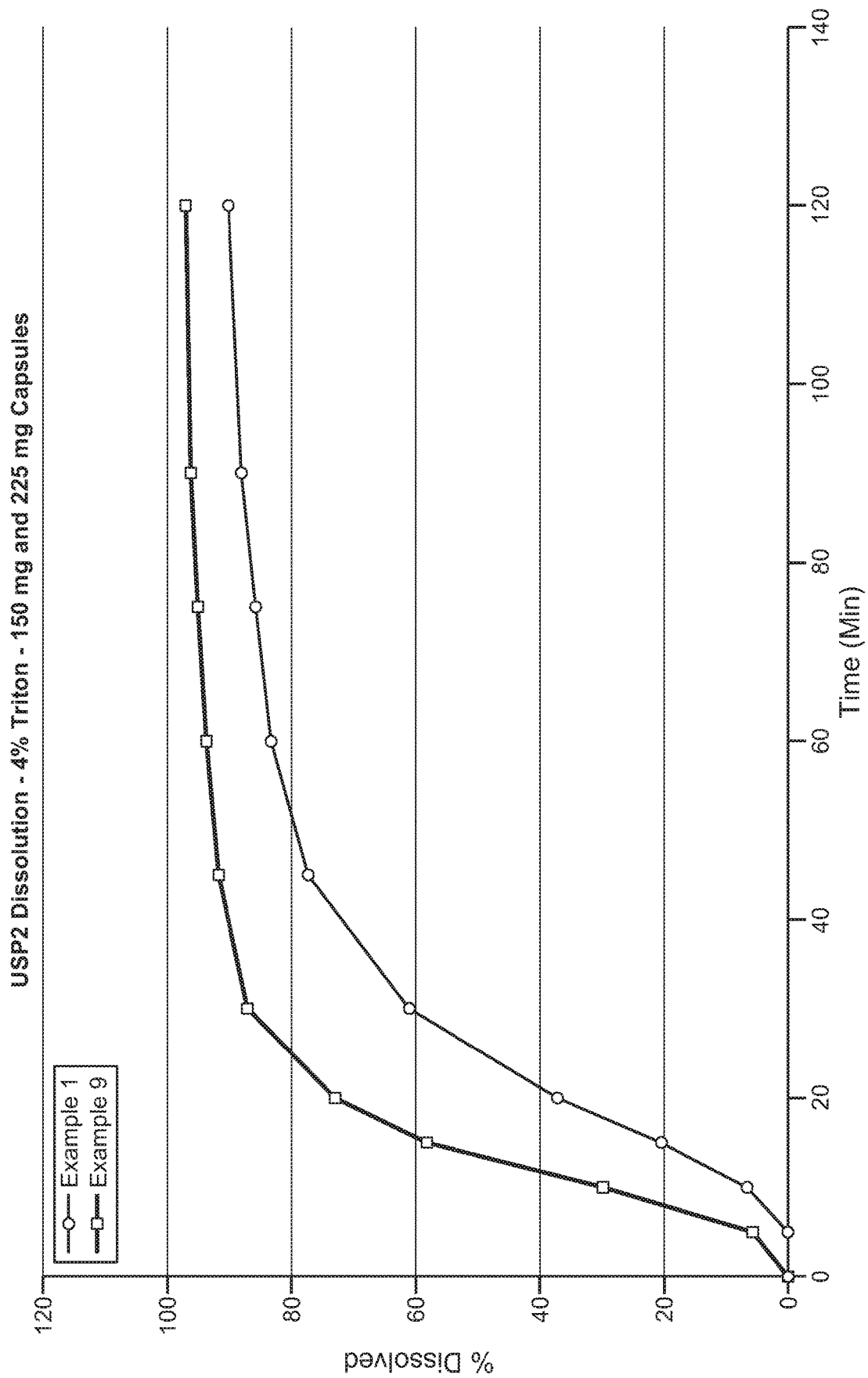
FIG. 3 illustrates the difference of dissolution results in Triton media (4% Triton/USP2) of capsules produced according to examples 1 and 9.

The term "active pharmaceutical ingredient" (or "API") denotes the compound or a pharmaceutically acceptable salt thereof in a pharmaceutical composition that has a particular biological activity.

The term "Biopharmaceutics Classification System" or "BCS" refers to the regulatory term for biopharmaceutic drug classification theorized by Amidon G L, Lennernäs H, Shah V P, Crison J R in *Pharm. Res.* 1995, 12 (3): 413-20 and described in the FDA BCS guidance.

The term "drop point refers to the temperature at which a composition passes from a semi-solid to a liquid state under specific test conditions.

The term "free base equivalent" refers to the weight of pharmaceutically acceptable salt of an active pharmaceutical ingredient form, thus calculated as free base form of active pharmaceutical ingredient form. For example, if an API is used in the form of a salt, reference to "50 mg of free base equivalent of the API" means the amount of salt that would be needed to provide 50 mg of the free base upon complete dissociation of the salt.

The term "hydrophilic-lipophilic balance" (HLB) value denotes the degree of hydrophilicity of a non-ionic surfactant. The HLB value is determined by the ratio between the molecular mass of the hydrophilic portion of the surfactant molecule and its overall molecular mass, as described by Griffin W. C., Journal of the Society of Cosmetic Chemists (1949) 1:311.

The term "pharmaceutically acceptable" denotes an attribute of a material which is useful in preparing a pharmaceutical composition that is generally safe, non-toxic, and neither biologically nor otherwise undesirable and is acceptable for veterinary as well as human pharmaceutical use.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, in particular hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition, these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyimine resins and the like. Particular pharmaceutically acceptable salts of compounds of formula (I) are the hydrochloride salts, methanesulfonic acid salts and citric acid salts. More particularly pharmaceutically acceptable salts of compounds of formula (I) are hydrochloride salts.

The term "pharmaceutical composition" (or "composition") denotes a mixture or solution comprising a therapeutically effective amount of an active pharmaceutical ingredient together with pharmaceutically acceptable excipients to be administered to a mammal, e.g., a human in need thereof.

The term "polyoxyethylene sorbitan fatty ester" denotes oleate esters of sorbitol and its anhydrides, typically copolymerized with ethylene oxide. Particular polyoxyethylene sorbitan fatty ester are polyoxyethylene 20 sorbitan monooleate also kwon as polysorbate 80 or Tween 80 (T80).

The term "polyoxylglyceride" refers to mixtures of monoesters, diesters and triesters of glycerol and monoesters and diesters of polyethylene glycols. Examples of polyoxylglycerides are caprylocaproyl polyoxylglyceride, a lauroyl polyoxylglyceride, a linoleoyl polyoxylglyceride, a oleoyl polyoxylglyceride or a stearoyl polyoxylglyceride. Particular examples of polyoxylglyceride lauroyl polyoxylglyceride. More particularly, the polyoxyliceride as surfactant A is a lauroyl polyoxylglyceride with a HLB of 14 and a drop point of 44° C., particularly lauroyl macrogol-32 glyceride, also known as lauroyl polyoxyl-32 glyceride, lauroyl macrogolglyceride, lauroyl polyoxylglyceride, polyoxyl glyceryl laurate, PEG glyceryl laurat, hydrogenated coconut oil PEG-32 esters or Gelucire 44/14.

The term "propylene glycol monolaurate" refers to a mixture of propylene glycol mono and diesters of lauric acid. Particular examples of propylene glycol monolaurate is propylene glycol monolaurate type II, wherein the content of monoesters is equal or more than 90% also known as lauroglycol 90 (LG90).

The term "tocopherol derivative" refers to tocopherol moiety linked, optionally via a linker, to a polymer or copolymer chain. Particular tocopherol derivatives are tocopherol polyethylene glycol. Further particular tocopherol derivative is vitamin E polyethylene glycol succinate. Furthermore particular tocopherol derivative is vitamin E polyethylene glycol succinate wherein the chain length of the polyethylene glycol chain is 1000, also known as TPGS, tocopherol polyethylene glycol succinate, α-Tocopherol polyethylene glycol succinate, Vitamin E PEG succinate, tocofersolan and tocophersolan.

Unless otherwise stated all percentages are given in weight percent of the total weight of the composition.

The present information provides a pharmaceutical composition comprising
  a) one or more active ingredients or pharmaceutically acceptable salt thereof,
  b) a non-ionic surfactant A solid at room temperature, and
  c) a non-ionic surfactant B liquid at room temperature, wherein the HLB of surfactants A and B are independently equal or greater than 8 and wherein the active ingredients or pharmaceutically acceptable salt thereof are dispersed in the matrix formed by the other ingredients.

A particular embodiment of the present invention is a pharmaceutical composition as described herein, wherein the active ingredients are dispersed in the matrix formed by surfactants A and B.

Also a particular embodiment of the present invention is a pharmaceutical composition as described herein, wherein the active ingredients are in a micronized form.

In a further particular embodiment of the present invention as described herein, the particle size of the micronized active ingredients is between 0.2 µm and 20 µm.

In a more particular embodiment of the present invention as described herein, the particle size of the micronized active ingredients is between 0.2 µm and 15 µm.

In a furthermore particular embodiment of the present invention as described herein, the particle size of the micronized active ingredients is between 0.2 µm and 8 µm.

A particular embodiment of the present invention is a pharmaceutical composition as described herein comprising only one active ingredients or pharmaceutically acceptable salt thereof.

Another embodiment of the present invention is a pharmaceutical composition as described herein, wherein one of the active ingredient or its pharmaceutically acceptable salt thereof is class III or IV drug according to the Biopharmaceutics Classification System.

A particular embodiment of the present invention is a pharmaceutical composition as described herein, wherein one of the active ingredient or its pharmaceutically acceptable salt thereof is class IV drug according to the Biopharmaceutics Classification System.

Another embodiment of the present invention is a pharmaceutical composition as described herein, wherein one of the active ingredients is a kinase inhibitor or pharmaceutically acceptable salt thereof.

A particular embodiment of the present invention is a pharmaceutical composition as described herein, wherein one of the active ingredients is an ALK inhibitor or pharmaceutically acceptable salt thereof.

A particular embodiment of the present invention is a pharmaceutical composition as described herein, wherein one of the active ingredient is 9-ethyl-6,6-dimethyl-8-(4-morpholin-4-yl-piperidin-1-yl)-11-oxo-6,11-dihydro-5H-benzo[b]carbazole-3-carbonitrile or pharmaceutically acceptable salt thereof.

A further particular embodiment of the present invention is a pharmaceutical composition as described herein, wherein one of the active ingredient is 9-ethyl-6,6-dimethyl-8-(4-morpholin-4-yl-piperidin-1-yl)-11-oxo-6,11-dihydro-5H-benzo[b]carbazole-3-carbonitrile or pharmaceutically acceptable salt thereof and is in crystalline form.

Another more particular embodiment of the present invention is a pharmaceutical composition as described herein, wherein one of the active ingredient is 9-ethyl-6,6-dimethyl-8-(4-morpholin-4-yl-piperidin-1-yl)-11-oxo-6,11-dihydro-5H-benzo[b]carbazole-3-carbonitrile hydrochloride.

Another particular embodiment of the present invention is a pharmaceutical composition as described herein, comprising from 20 to 250 mg of the free base equivalent of 9-ethyl-6,6-dimethyl-8-(4-morpholin-4-yl-piperidin-1-yl)-11-oxo-6,11-dihydro-5H-benzo[b]carbazole-3-carbonitrile.

Another further particular embodiment of the present invention is a pharmaceutical composition as described herein, comprising from 20 to 225 mg of the free base equivalent of 9-ethyl-6,6-dimethyl-8-(4-morpholin-4-yl-piperidin-1-yl)-11-oxo-6,11-dihydro-5H-benzo[b]carbazole-3-carbonitrile.

Another more particular embodiment of the present invention is a pharmaceutical composition as described herein, comprising from 100 to 200 mg of the free base equivalent of 9-ethyl-6,6-dimethyl-8-(4-morpholin-4-yl-piperidin-1-yl)-11-oxo-6,11-dihydro-5H-benzo[b]carbazole-3-carbonitrile.

Another furthermore particular embodiment of the present invention is a pharmaceutical composition as described herein, comprising from 125 to 175 mg of the free base equivalent of 9-ethyl-6,6-dimethyl-8-(4-morpholin-4-yl-piperidin-1-yl)-11-oxo-6,11-dihydro-5H-benzo[b]carbazole-3-carbonitrile.

Another even more particular embodiment of the present invention is a pharmaceutical composition as described herein, comprising 150 mg of the free base equivalent of 9-ethyl-6,6-dimethyl-8-(4-morpholin-4-yl-piperidin-1-yl)-11-oxo-6,11-dihydro-5H-benzo[b]carbazole-3-carbonitrile.

Another even more particular embodiment of the present invention is a pharmaceutical composition as described herein, comprising 161 mg of 9-ethyl-6,6-dimethyl-8-(4-morpholin-4-yl-piperidin-1-yl)-11-oxo-6,11-dihydro-5H-benzo[b]carbazole-3-carbonitrile hydrochloride.

Another embodiment of the present invention is a pharmaceutical composition as described herein, characterized in that the drop point of the pharmaceutical composition is comprised between 32 and 41° C.

Another particular embodiment of the present invention is a pharmaceutical composition as described herein, characterized in that the drop point of the pharmaceutical composition is comprised between 35 and 39° C.

Also a particular embodiment of the present invention is a pharmaceutical composition as described herein, wherein the surfactant A has a HLB equal or greater than 12.

Another particular embodiment of the present invention is a pharmaceutical composition as described herein, wherein the surfactant B has a HLB equal or greater than 12.

Also an embodiment of the present invention is a pharmaceutical composition as described herein, wherein the surfactant A is a tocopherol derivative or polyoxylglyceride.

A particular embodiment of the present invention is a pharmaceutical composition as described herein, wherein the surfactant A is a tocopherol derivative or a caprylocaproyl polyoxylglyceride, a lauroyl polyoxylglyceride, a linoleoyl polyoxylglyceride, a oleoyl polyoxylglyceride or a stearoyl polyoxylglyceride.

In a further particular embodiment of the present invention as described herein, wherein the polyoxylglyceride has a drop point comprised between 40 and 48° C.

A furthermore particular embodiment of the present invention is a pharmaceutical composition as described herein, wherein the polyoxylglyceride has a drop point comprised between 40 and 46° C.

A more particular embodiment of the present invention is a pharmaceutical composition as described herein, wherein the lauroyl polyoxylglyceride has a hydrophilic balance comprised between 12-15 and a drop point comprised between 40 and 46° C.

A further particular embodiment of the present invention is a pharmaceutical composition as described herein, wherein the surfactant A is a tocopherol derivative or a lauroyl polyoxylglyceride.

A particular embodiment of the present invention is a pharmaceutical composition as described herein, wherein the tocopherol derivative is a tocopherol polyethylene glycol ester.

A further particular embodiment of the present invention is a pharmaceutical composition as described herein, wherein the tocopherol derivative is vitamin E polyethylene glycol succinate.

A furthermore particular embodiment of the present invention is a pharmaceutical composition as described herein, wherein the tocopherol derivative is vitamin E polyethylene glycol succinate wherein the chain length of the polyethylene glycol chain is 1000.

A more particular embodiment of the present invention is a pharmaceutical composition as described herein, wherein the lauroyl polyoxylglyceride has a HLB of 14 and a drop point of 44° C.

An even more particular embodiment of the present invention is a pharmaceutical composition as described herein, wherein the surfactant A is vitamin E polyethylene glycol succinate wherein the chain length of the polyethylene glycol chain is 1000 or a lauroyl polyoxylglyceride has a HLB of 14 and a drop point of 44° C.

Also an embodiment of the present invention is a pharmaceutical composition as described herein, wherein the surfactant B is a caprylocaproyl polyoxylglyceride, a polyoxyethylene sorbitan fatty acid ester, propylene glycol monolaurate type I or propylene glycol monolaurate type II.

A particular embodiment of the present invention is a pharmaceutical composition as described herein, wherein surfactant B is a polyoxyethylene sorbitan fatty acid ester or propylene glycol monolaurate type II.

A further particular embodiment of the present invention is a pharmaceutical composition as described herein, wherein the polyoxyethylene sorbitan fatty acid ester is selected from polyoxyethylene 20 sorbitan monolaurate, polyoxyethylene (4) sorbitan monolaurate, polyoxyethylene 20 sorbitan monopalmitate, polyoxyethylene 20 sorbitan monostearate, polyoxyethylene (4) sorbitan monostearate, polyoxyethylene 20 sorbitan tristearate, polyoxyethylene 20 sorbitan monooleate, polyoxyethylene (5) sorbitan monooleate, polyoxyethylene 20 sorbitan trioleate and polyoxyethylene 20 sorbitan monoisostearate.

A more particular embodiment of the present invention is a pharmaceutical composition as described herein, wherein the polyoxyethylene sorbitan fatty acid ester is selected from polyoxyethylene 20 sorbitan monolaurate, polyoxyethylene 20 sorbitan monopalmitate, polyoxyethylene 20 sorbitan monostearate, polyoxyethylene 20 sorbitan monooleate and polyoxyethylene 20 sorbitan monoisostearate.

A furthermore particular embodiment of the present invention is a pharmaceutical composition as described herein, wherein the polyoxyethylene sorbitan fatty acid ester is polyoxyethylene 20 sorbitan monooleate.

Another particular embodiment of the present invention is a pharmaceutical composition as described herein, comprising surfactant A and B in a ratio in weight from between 1:1: to 8:2.

A furthermore particular embodiment of the present invention is a pharmaceutical composition as described herein, comprising surfactant A and B in a ratio in weight of 7:3.

A particular embodiment of the present invention is a pharmaceutical composition as described herein, comprising
- 9-ethyl-6,6-dimethyl-8-(4-morpholin-4-yl-piperidin-1-yl)-11-oxo-6,11-dihydro-5H-benzo[b]carbazole-3-carbonitrile or pharmaceutically acceptable salt thereof;
- vitamin E polyethylene glycol succinate; and
- polyoxyethylene 20 sorbitan monooleate.

A further particular embodiment of the present invention is a pharmaceutical composition as described herein, comprising
- 4 to 50% in weight of 9-ethyl-6,6-dimethyl-8-(4-morpholin-4-yl-piperidin-1-yl)-11-oxo-6,11-dihydro-5H-benzo[b]carbazole-3-carbonitrile, hydrochloride;
- 35 to 70% of vitamin E polyethylene glycol succinate; and 15 to 30% in weight of polyoxyethylene 20 sorbitan monooleate.

A more particular embodiment of the present invention is a pharmaceutical composition as described herein, comprising
- 20 to 225 mg of 9-ethyl-6,6-dimethyl-8-(4-morpholin-4-yl-piperidin-1-yl)-11-oxo-6,11-dihydro-5H-benzo[b]carbazole-3-carbonitrile or pharmaceutically acceptable salt thereof;
- 150 to 300 mg of vitamin E polyethylene glycol succinate; and
- 50 to 150 mg of polyoxyethylene 20 sorbitan monooleate.

A furthermore particular embodiment of the present invention is a pharmaceutical composition as described herein, comprising
- 150 mg of free base equivalent of 9-ethyl-6,6-dimethyl-8-(4-morpholin-4-yl-piperidin-1-yl)-11-oxo-6,11-dihydro-5H-benzo[b]carbazole-3-carbonitrile;
- 245 mg of vitamin E polyethylene glycol succinate; and
- 105 mg of polyoxyethylene 20 sorbitan monooleate.

An even more particular embodiment of the present invention is a pharmaceutical composition as described herein, comprising
- 161 mg of 9-ethyl-6,6-dimethyl-8-(4-morpholin-4-yl-piperidin-1-yl)-11-oxo-6,11-dihydro-5H-benzo[b]carbazole-3-carbonitrile hydrochloride;
- 245 mg of vitamin E polyethylene glycol succinate; and
- 105 mg of polyoxyethylene 20 sorbitan monooleate.

Another embodiment of the present invention is a pharmaceutical composition as described herein, obtainable by
a) melting surfactant A;
b) mixing melted surfactant A and liquid surfactant B; and
c) suspending the active ingredients or pharmaceutically acceptable salts thereof in the obtained mixture.

Also an embodiment of the present invention is a capsule comprising a pharmaceutical composition as described herein.

Another embodiment of the present invention is the use of a pharmaceutical composition as described herein for preparing a medicament for the treatment or prophylaxis of cancer.

Another particular embodiment of the present invention is the use of a pharmaceutical composition as described herein for preparing a medicament for the treatment or prophylaxis of lung cancer.

Another further particular embodiment of the present invention is the use of a pharmaceutical composition as described herein for preparing a medicament for the treatment or prophylaxis of non-small cells lung cancer.

Another embodiment of the present invention is the use of a pharmaceutical composition as described herein for the treatment or prophylaxis of cancer.

Another particular embodiment of the present invention is the use of a pharmaceutical composition as described herein for the treatment or prophylaxis of lung cancer.

Another further particular embodiment of the present invention is the use of a pharmaceutical composition as described herein for the treatment or prophylaxis of non-small cells lung cancer.

Another embodiment of the present invention is a pharmaceutical composition as described herein for the treatment or prophylaxis of cancer.

Another particular embodiment of the present invention is a pharmaceutical composition as described herein for the treatment or prophylaxis of lung cancer.

Another further particular embodiment of the present invention is a pharmaceutical composition as described herein for the treatment or prophylaxis of non-small cells lung cancer.

Also an embodiment of the present invention is a process for preparing a pharmaceutical composition as described herein, comprising steps a), b) and c)
a) melting surfactant A;
b) mixing melted surfactant A and liquid surfactant B; and
c) suspending the active ingredients or pharmaceutically acceptable salts thereof in the obtained mixture.

Manufacturing Process:

In the examples 1 to 9, the API refers to 9-ethyl-6,6-dimethyl-8-(4-morpholin-4-yl-piperidin-1-yl)-11-oxo-6,11-dihydro-5H-benzo[b]carbazole-3-carbonitrile hydrochloride.

The capsules used were Licaps capsules size 1 according to M. J. Rathbone, J. Hadgraft, M. S. Roberts (Eds.), Modified-Release Drug Delivery Technology, Marcel Dekker, New York, 2003, pp. 177-188 manufactured and provided by Capsugel, France.

The examples were prepared according to the following manufacturing process:

a) Preparation of the Fill Mass

Surfactant A is heated in a closed container at 50-55° C. until it is completely molten. Surfactant B is at the same time equilibrated to RT. Both excipient containers are stirred and the required amounts are removed. They are combined in a blending vessel and shortly stirred until they are homogenous.

After the fill mass has cooled to approximately 42-45° C., the micronized API is added in portions while the fill mass is stirred with a propeller type stirrer. Dependent on the batch size, the blending vessel needs to be maintained at 42° C. minimum. The suspension is stirred until homogenous.

Depending of the blending vessel an additional degassing step by vacuum is done or else a longer stirring time should be used to remove any air that has been stirred in during API addition.

b) Encapsulation/Sealing/Drying

The fill mass is transferred to the hopper of a CFS encapsulation machine (manufacturer: Capsugel, France). The hopper is heated to 40-45° C., keeping the fill mass in a temperature range of 38-43° C. The heating of the pump unit is selected at 37° C. The CFS carries out encapsulation, sealing and drying in a single process run. The sealed capsules are stored at room temperature which leads to a solidification of the fill matrix. By this the API gets entrapped in a finely dispersed state.

Dissolution Test Methods

Method USP2

Dissolution Parameters

| | |
|---|---|
| Apparatus | Ph. Eur. rotating paddle apparatus (USP apparatus 2) |
| Medium | Simulated gastric fluid (SGF) pH 1.2 + 4% Triton X-100 |
| De-aeration | None |
| Volume | 900 mL |
| Temperature | 37° C. |

-continued

| | |
|---|---|
| Paddle speed | 100 rpm |
| Units tested | 6 × 1 unit |
| Sampling | 10 mL (manual sampling) without medium replacement after 5, 10, 15, 20, 30, 45, 60, 75, 90 and 120 min. Time can be adapted depending on the observed release rate. |
| Position | Samples are withdrawn from a zone midway between the surface of the dissolution medium and the top of the rotating paddle, not less than 1 cm from the vessel wall. For automated sampling (e.g. Sotax AT7 or AT70) 25 mL of the test solution are pumped through the circuit before the sampling times to pre-rinse the sampling lines and filters. |
| Pre-Filter | Cannula Filter 35 μm (e.g. PSFIL035-SX-100) |
| Filter | Acrodisc ® 25 mm Syringe Filter with 1 μm glass fibre membrane (Pall Corporation; #PN4529); discard the first 3 mL. |
| Sinker | Japanese Sinker (Vendor No.: 65-190-012) |
| Method of Analysis | HPLC at 230 nm |

Chemicals and Reagents for the Dissolution Medium

Reagents and chemicals of equivalent quality may be used.

| Chemical/Reagent | Quality/Purity | Supplier Code |
|---|---|---|
| Water | Deionized Water | — |
| HCl 37% | For analysis | Merck 1.00317 |
| Triton X-100 | For analysis | Merck 1.08603 |
| NaCl | For analysis | Merck 1.06404 |

Dissolution Media Preparation

Alternative preparation and dilution schemes can be used.

Simulated gastric fluid (SGF) pH 1.2+4% Triton X-100

Accurately weigh 4 g of sodium chloride and dissolve in approximately 1 L of water. Add 7 mL of concentrated 37% Hydrochloride fuming acid. Weigh 40 g of Triton X-100, transfer to solution and mix to dissolve.

Determination by High Performance Liquid Chromatography

Instrument and Conditions (Equivalent instrumentation and appropriate operating conditions may be used.)

| | |
|---|---|
| Pump | Agilent 1200 (binary pump) |
| Injection System | Agilent 1200 |
| Detector | Agilent 1200 UV/VIS with 10 mm cell |
| Degasser | Agilent |
| Column | Steel column 4.6 × 150 mm |
| Stationary Phase | Sunfire C18 (Waters), 3.5 μm |
| Column temperature | 35° C. |
| Autosampler temperature | Room Temperature uncontrolled |
| Detector setting | UV, 230 nm, Bandwidth: 4 nm, Path length: 1 cm |
| Flow rate | 1.0 mL/min |
| Wavelength | 230 nm |
| Injection volume | 10 μL for 150 mg of free base equivalent of API 7.5 μL for 200 mg of free base equivalent of API |
| Run time | 5 minutes |
| Mobile Phase | Water/Acetonitrile/TFA 1200/800/1 v/v isocratic conditions |
| Rheodyne rinsing | 1200 Water/800 Acetonitrile |
| Sampler Tray temperature | Room Temperature uncontrolled |

Column cleaning: Wash the column after the measuring of a maximum of 6 sample solutions and 1 reference solution.

This column cleaning is performed under the conditions stated below.

Mobile Phase A: Water/acetonitrile/trifluoroacetic acid (1200:800:1)

Mobile Phase B: Acetonitrile/trifluoroacetic acid (2000:1)

Mobile Phase Flow: Control the concentration gradient by varying the percentages of mobile phase A and mobile phase B as shown below.

Gradient:

| Time after injection (min) | Mobile phase A (vol %) 0 100 | Mobile phase B (vol %) |
|---|---|---|
| 0~4 | 0 | 100 |
| 4~4.01 | 0 → 100 | 100 → 0 |
| 4.01~13 | 100 | 0 |

Chemicals and Reagents for the HPLC

Reagents and chemicals of equivalent quality may be used.

| Chemical/Reagent | Quality/Purity | Supplier Code |
|---|---|---|
| Water | HPLC grade, deionized | — |
| Acetonitrile | HPLC grade | Merck 1.00030.2500 |
| TFA | HPLC grade | Merck 8.08260 |

HPLC Mobile Phase Preparation

Mix 1200 mL of HPLC grade water and 800 mL of acetonitrile, add 1 mL of TFA in a 2l volumetric flask. Degas prior to use.

Column Cleaning

Mobile Phase A

Mix 1200 mL of HPLC grade water and 800 mL of acetonitrile, add 1 mL of TFA in a 2l volumetric flask. Degas prior to use.

Mobile Phase B

Mix 2000 mL of acetonitrile, add 1 mL of TFA in a 2l volumetric flask. Degas prior to use.

Peaks of Interest:

| Component | Approximate Retention Time (minutes) | Response Factor (RF) |
|---|---|---|
| Alectinib | 3.0 | 1.00 |

Run time: 5 minutes

Reference Solution (Prepare in Duplicate.)

Equivalent quantities and volumes may be used.

Reference Solution for 150 mg Free Base Capsule Strength:

Weigh 9 mg of Alectinib reference substance (hydrochloride salt) into a 50 mL amber volumetric flask. Add 5 mL of Acetonitrile:water (1:1 v/v) and sonicate until dissolved. Dilute to volume with dissolution media, mix well.

Stability of Reference Solution:

Reference solution in amber glass flask is stable for 5 days at RT.

Stability of Sample Solution:

Sample solution in HPLC vials is stable for 11 days in the autosampler at RT.

HPLC System Suitability Test:

The Relative Standard Deviation (Srel) of the response factors calculated from a minimum of 6 Reference Solution injections (minimum 3 injections of reference solution A and B) must be less than or equal to 2.0%. If the Srel is more than 2.0%, the cause must be investigated. The SST can be re-evaluated with the same raw data, ignoring the injection which failed if the root cause is found and if a minimum of 6 injections are available. If not, the complete analysis has to be performed again.

Calculations

Dissolution with volume correction, drawn volumes not replaced

Principle: area evaluation with external standard

% dissolved corrected:

$$\% \ D(t) = \% \ D_{nc}(t) \times \frac{V_M - (t-1) \times V_p}{V_M} + \sum_{n=1}^{t-1} \% \ D_{nc}(n) \times \frac{V_p}{V_M} \quad (1)$$

The equation applies for dissolution calculation without media replacement

Assay Determination by UV/HPLC % Dissolved Non-Corrected $$\% \ D_{nc}(t) = \frac{A_M \times E_{ST} \times P \times V_M}{A_{ST} \times L \times V_{ST}}$$

t=Number of drawn sample (t=1 to x)
% D(t)=% Dissolution for sample no. t
% $D_{nc}$(t)=% Uncorrected dissolution for sample no. t
$A_M$=Peak area of the sample solution
$A_{St}$=Peak area of the reference solution
$E_{St}$=Mass of the reference substance (mg)
P=Purity of the reference substance in %
L=Label Claim of the sample (mg)
$V_M$=Volume of dissolution medium (ml)
$V_P$=Volume of drawn sample (ml)
$V_{ST}$=Dilution of the reference solution (ml)

Dissolution Test—USP4

Dissolution Parameters

| | |
|---|---|
| Apparatus | Ph. Eur. Flow through cell apparatus (USP apparatus 4) |
| Medium | FeSSIF (Fed State Simulated Intestinal Fluid) pH 5.0 |
| De-aeration | None |
| Volume | 1000 mL |
| Temperature | 37° C. |
| Dosage (mg) | Equivalent to 20 mg drug substance |
| Mode | closed |
| Loading | Type 1 |
| Cell type | 22.6 mm tablet cell |
| Flow (ml/min) | 25 |
| Duration (min) | 120 |
| Sampling times (min) | 5, 10, 15, 30, 45, 60, 90, 120 |
| Filter | GF/C |
| Quantification | HPLC at 230 nm |

Chemicals and Reagents for the Dissolution Medium

Reagents and chemicals of equivalent quality may be used.

| Chemical/Reagent | Quality/Purity | Supplier Supplier Code |
|---|---|---|
| Water | Deionized Water | — |
| NaOH | For analysis | |
| Glacial acetic acid | For analysis | |
| NaCl | For analysis | Merck 1.06404 |
| SIF powder V1 | For analysis | |

Dissolution Media Preparation

Alternative preparation and dilution schemes can be used.

Fed State Simulated Intestinal Fluid pH 5.0

Dissolve (accurately weighed):

4.040 g of NaOH (pellets), 8.650 g of Glacial Acetic Acid, 11.874 g of NaCl in about 0.900 L of purified water. Adjust the pH to 5 with either 1 N NaOH or 1 N HCl. Make up to volume (1.000 L) with purified water at room temperature. Add 11.200 g (accurately weighed) of SIF Powder Original to about 0.5 L of buffer. Stir until powder is completely dissolved. Make up to volume (1.000 L) with buffer at room temperature.

Determination by High Performance Liquid Chromatography

Performed according to Method USP2

Reference Solution (Prepare in Duplicate.)

Performed according to Method USP2 using the dissolution medium described there (SGF+4% Triton-X).

HPLC System Suitability Test

Performed according to Method USP2

Calculations

Performed according to Method USP2

Drop Point Determination

Equipment: Mettler Toledo FP 90

Measuring chamber: FP 83 HT

Method Description:

Equipment is tested with Benzophenone as reference substance.

The sample is inserted in the measuring cell. The oven is heated about 5° C. below the estimated drop point at a heat rate of 1° C./minute.

As soon as there is a drop released from the 2.8 mm opening, the equipment will register the drop point of the sample, as the drop will pass a light beam during falling from the opening.

EXAMPLE 1

| Ingredient | | Mass/unit (mg) | Amount/Unit (%) |
|---|---|---|---|
| API | | 161 | 31.51 |
| Surfactant A | vitamin E polyethylene glycol succinate | 245 | 47.95 |
| Surfactant B | Polysorbate 80 | 105 | 20.55 |
| Capsule | Licaps size 1 | | |
| Total | | 511 | 100.00 |

EXAMPLE 2

| Ingredient | | Mass/unit (mg) | Amount/Unit (%) |
|---|---|---|---|
| API | | 161 | 31.51 |
| Surfactant A | vitamin E polyethylene glycol succinate | 280 | 54.79 |
| Surfactant B | Polysorbate 80 | 70 | 13.70 |
| Capsule | Licaps size 1 | | |
| Total | | 511 | 100.00 |

EXAMPLE 3

| Ingredient | | Mass/unit (mg) | Amount/Unit (%) |
|---|---|---|---|
| API | | 161 | 31.51 |
| Surfactant A | vitamin E polyethylene glycol succinate | 245 | 47.95 |
| Surfactant B | Propylene glycol monolaurate type II | 105 | 20.55 |
| Capsule | Licaps size 1 | | |
| Total | | 511 | 100.00 |

EXAMPLE 4

| Ingredient | | Mass/unit (mg) | Amount/Unit (%) |
|---|---|---|---|
| API | | 161 | 31.51 |
| Surfactant A | vitamin E polyethylene glycol succinate | 280 | 54.79 |
| Surfactant B | Propylene glycol monolaurate type II | 70 | 13.70 |
| Capsule | Licaps size 1 | | |
| Total | | 511 | 100.00 |

EXAMPLE 5

| Ingredient | | Mass/unit (mg) | Amount/Unit (%) |
|---|---|---|---|
| API | | 161 | 31.51 |
| Surfactant A | Lauroyl polyoxylglyceride (Gelucire 44/14) | 245 | 47.95 |
| Surfactant B | Polysorbate 80 | 105 | 20.55 |
| Capsule | Licaps size 1 | | |
| Total | | 511 | 100.00 |

EXAMPLE 6

| Ingredient | | Mass/unit (mg) | Amount/Unit (%) |
|---|---|---|---|
| API | | 161 | 31.51 |
| Surfactant A | Lauroyl polyoxylglyceride (Gelucire 44/14) | 210 | 41.10 |
| Surfactant B | Polysorbate 80 | 140 | 27.40 |
| Capsule | Licaps size 1 | | |
| Total | | 511 | 100.00 |

EXAMPLE 7

| Ingredient | | Mass/unit (mg) | Amount/Unit (%) |
|---|---|---|---|
| API | | 161 | 31.51 |
| Surfactant A | Lauroyl polyoxylglyceride (Gelucire 44/14) | 175 | 34.25 |
| Surfactant B | Polysorbate 80 | 175 | 34.25 |
| Capsule | Licaps size 1 | | |
| Total | | 511 | 100.00 |

EXAMPLE 8

| Ingredient | | Mass/unit (mg) | Amount/Unit (%) |
|---|---|---|---|
| API | | 161 | 31.51 |
| Surfactant A | Lauroyl polyoxylglyceride (Gelucire 44/14) | 245 | 47.95 |
| Surfactant B | Propylene glycol monolaurate type II | 105 | 20.55 |
| Capsule | Licaps size 1 | | |
| Total | | 511 | 100.00 |

EXAMPLE 9

| Ingredient | | Mass/unit (mg) | Amount/Unit (%) |
|---|---|---|---|
| API | | 241.5 | 46.76 |
| Surfactant A | vitamin E polyethylene glycol succinate | 192.5 | 37.27 |
| Surfactant B | Polysorbate 80 | 82.5 | 15.97 |
| Capsule | Licaps size 1 | | |
| Total | | 516.5 | 100.00 |

EXAMPLE 10

| Ingredient | | Mass/unit (mg) | Amount/Unit (%) |
|---|---|---|---|
| API | | 193 | 37.62 |
| Surfactant A | vitamin E polyethylene glycol succinate | 224 | 43.66 |
| Surfactant B | Polysorbate 80 | 96 | 18.71 |
| Capsule | Licaps size 1 | | |
| Total | | 513 | 100.00 |

EXAMPLE 11

| Ingredient | | Mass/unit (mg) | Amount/Unit (%) |
|---|---|---|---|
| API | | 193 | 39.99 |
| Surfactant A | vitamin E polyethylene glycol succinate | 202.7 | 42.00 |
| Surfactant B | Polysorbate 80 | 86.9 | 18.01 |
| Capsule | Licaps size 1 | | |
| Total | | 482.6 | 100.00 |

EXAMPLE 12

| Ingredient | | Mass/unit (mg) | Amount/Unit (%) |
|---|---|---|---|
| API | | 225.4 | 43.69 |
| Surfactant A | vitamin E polyethylene glycol succinate | 203.3 | 39.41 |
| Surfactant B | Polysorbate 80 | 87.2 | 16.90 |
| Capsule | Licaps size 1 | | |
| Total | | 515.9 | 100.00 |

The invention claimed is:

1. A pharmaceutical composition comprising:
   a) 9-ethyl-6,6-dimethyl-8-(4-morpholin-4-yl-piperidin-1-yl)-11-oxo-6,11-dihydro-5H-benzo[b]carbazole-3-carbonitrile hydrochloride,
   b) a non-ionic surfactant A that is a solid at room temperature that is vitamin E polyethylene glycol succinate, and
   c) a non-ionic surfactant B that is liquid at room temperature that is polysorbate 80, wherein the HLB of surfactants A and B are independently equal or greater than 8 and wherein 9-ethyl-6,6-dimethyl-8-(4-morpholin-4-yl-piperidin-1-yl)-11-oxo-6,11-dihydro-5H-benzo[b]carbazole-3-carbonitrile hydrochloride is dispersed in the matrix formed by surfactants A and B.

2. The pharmaceutical composition according to claim 1, comprising 161 mg of 9-ethyl-6,6-dimethyl-8-(4-morpholin-4-yl-piperidin-1-yl)-11-oxo-6,11-dihydro-5H-benzo[b]carbazole-3-carbonitrile hydrochloride.

3. The pharmaceutical composition according to claim 1, characterized in that the drop point of the pharmaceutical composition is between 32 and 41° C.

4. The pharmaceutical composition according to claim 1, wherein surfactant A is vitamin E polyethylene glycol succinate wherein the chain length of the polyethylene glycol chain is 1000.

5. The pharmaceutical composition according to claim 1, comprising surfactant A and B in a ratio in weight from between 1:1 to 8:2.

6. The pharmaceutical composition according to claim 1, wherein the 9-ethyl-6,6-dimethyl-8-(4-morpholin-4-yl-piperidin-1-yl)-11-oxo-6,11-dihydro-5H-benzo[b]carbazole-3-carbonitrile hydrochloride is in a micronized form.

7. The pharmaceutical composition according to claim 6, wherein the particle size of the micronized 9-ethyl-6,6-dimethyl-8-(4-morpholin-4-yl-piperidin-1-yl)-11-oxo-6,11-dihydro-5H-benzo[b]carbazole-3-carbonitrile hydrochloride is between 0.2 µm and 20 µm.

8. The pharmaceutical composition according to claim 6, wherein the particle size of the micronized 9-ethyl-6,6-dimethyl-8-(4-morpholin-4-yl-piperidin-1-yl)-11-oxo-6,11-dihydro-5H-benzo[b]carbazole-3-carbonitrile hydrochloride is between 0.2 µm and 15 µm.

9. The pharmaceutical composition according to claim 6, wherein the particle size of the micronized 9-ethyl-6,6-dimethyl-8-(4-morpholin-4-yl-piperidin-1-yl)-11-oxo-6,11-dihydro-5H-benzo[b]carbazole-3-carbonitrile hydrochloride is between 0.2 µm and 8 µm.

10. The pharmaceutical composition according to claim 1, comprising only one active ingredient or pharmaceutically acceptable salt thereof, which is 9-ethyl-6,6-dimethyl-8-(4-morpholin-4-yl-piperidin-1-yl)-11-oxo-6,11-dihydro-5H-benzo[b]carbazole-3-carbonitrile hydrochloride.

11. The pharmaceutical composition according to claim 1, comprising from 20 to 250 mg of the free base equivalent of 9-ethyl-6,6-dimethyl-8-(4-morpholin-4-yl-piperidin-1-yl)-11-oxo-6,11-dihydro-5H-benzo[b]carbazole-3-carbonitrile hydrochloride.

12. The pharmaceutical composition according to claim 1, comprising from 20 to 225 mg of the free base equivalent of 9-ethyl-6,6-dimethyl-8-(4-morpholin-4-yl-piperidin-1-yl)-11-oxo-6,11-dihydro-5H-benzo[b]carbazole-3-carbonitrile hydrochloride.

13. The pharmaceutical composition according to claim 1, comprising from 100 to 200 mg of the free base equivalent of 9-ethyl-6,6-dimethyl-8-(4-morpholin-4-yl-piperidin-1-yl)-11-oxo-6,11-dihydro-5H-benzo[b]carbazole-3-carbonitrile hydrochloride.

14. The pharmaceutical composition according to claim 1, comprising from 125 to 175 mg of the free base equivalent of 9-ethyl-6,6-dimethyl-8-(4-morpholin-4-yl-piperidin-1-yl)-11-oxo-6,11-dihydro-5H-benzo[b]carbazole-3-carbonitrile hydrochloride.

15. The pharmaceutical composition according to claim 1, characterized in that the drop point of the pharmaceutical composition is between 35 and 39° C.

16. The pharmaceutical composition according to claim 1, comprising surfactant A and B in a ratio in weight of 7:3.

17. The pharmaceutical composition according to claim 1, comprising;
   20 to 225 mg of the free base equivalent of 9-ethyl-6,6-dimethyl-8-(4-morpholin-4-yl-piperidin-1-yl)-11-oxo-6,11-dihydro-5H-benzo[b]carbazole-3-carbonitrile hydrochloride,
   150 to 300 mg of vitamin E polyethylene glycol succinate, and
   50 to 150 mg of polysorbate 80.

18. The pharmaceutical composition according to claim 1, comprising:
150 mg of free base equivalent of 9-ethyl-6,6-dimethyl-8-(4-rnorpholin-4-yl-piperidin-l -yl)-11-oxo-6,11-dihydro-5H-benzo[b]carbazole-3-caronitrile hydrochloride,
245 mg of vitamin E polyethylene glycol succinate, and
105 mg of polysorbate 80.

19. The pharmaceutical composition according to claim 1, comprising:
161 mg of 9-ethyl-6,6-dimethyl-8-(4-morpholin-4-yl-piperidin-l-yl)-11-oxo-6,11-dihydro -5H-benzo[b]carbazole-3-carbonitrile hydrochloride,
245 mg of vitamin E polyethylene glycol succinate, and
105 mg of polysorbate 80.

20. A pharmaceutical composition comprising:
a) 9-ethyl-6,6-dimethyl-8-(4-morpholin-4-yl-piperidin-l -yl)-11-oxo-6,11-dihydro-5H-benzo[b]carbazole-3-carbonitrile hydrochloride,
b) a non-ionic surfactant A that is a solid at room temperature that is vitamin E polyethylene glycol succinate, and
c) a non-ionic surfactant B that is liquid at room temperature that is polysorbate 80,
wherein the HLB of surfactants A and B are independently equal or greater than 8,
wherein 9-ethyl-6,6-dimethyl-8-(4-morpholin-4-yl-piperidin-l -yl)-11-oxo-6,11-dihydro-5H-benzo[b]carbazole-3-carbonitrile hydrochloride is dispersed in the matrix formed by surfactants A and B, and
wherein the pharmaceutical composition is obtainable by:
a) melting surfactant A,
b) mixing melted surfactant A and liquid surfactant B, and
c) suspending 9-ethyl-6,6-dimethyl-8-(4-morpholin-4-yl-piperidin-1-yl)-11-oxo-6,11-dihydro-5H-benzo[b]carbazole-3-carbonitrile hydrochloride in the obtained mixture.

21. A pharmaceutical composition comprising:
a) 9-ethyl-6,6-dimethyl-8-(4-morpholin-4-yl-piperidin-1-yl)-1 1-oxo-6, 1 1-dihydro-5H-benzo[b]carbaxole-3-carbonitrile hydrochloride,
b) a non-ionic surfactant A that is a solid at room temperature that is lauroyl polyoxylglyceride, and
c) a non-ionic surfactant B that is liquid at room temperature that is polysorbate 80,
wherein the HLB of surfactants A and B are independently equal or greater than 8 and
wherein 9-ethyl-6,6-dimethyl-8-(4-morpholin-4-yl-piperidin-1-yl)-1 1-oxo-6, 1 1-dihydro-5H-benzo[b]carbazole-3-carbonitrile hydrochloride is dispersed in the matrix formed by surfactants A and B.

22. The pharmaceutical composition according to claim 21, comprising 161 mg of 9-ethyl-6,6-dimethyl-8-(4-morpholin-4-yl-piperidin-1-yl)-1 1-oxo-6,1 1-dihydro-5H-benzo[b]carbazole-3-carbonitrile hydrochloride.

23. The pharmaceutical composition according to claim 21, characterized in that the drop point of the pharmaceutical composition is between 32 and 41° C.

24. A pharmaceutical composition according to claim 21, wherein surfactant A is lauroyl polyoxylglyceride that has a hydrophilic balance comprised between 12-15 and a drop point comprised between 40 and 46° C.

25. The pharmaceutical composition according to claim 21, comprising surfactant A and B in a ratio in weight from between 1:1 to 8:2.

26. The pharmaceutical composition according to claim 21, wherein the 9-ethyl-6,6-dimethyl-8-(4-morpholin-4-yl-piperidin-1-yl)-1 1-oxo-6,1 1-dihydro-5H-benzo[b]carbazole-3-carbonitrile hydrochloride is in a micronized form.

27. The pharmaceutical composition according to claim 26, wherein the particle size of the micronized 9-ethyl-6,6-dimethyl-8-(4-morpholin-4-yl-piperidin-1-yl)-1 1-oxo-6,1 1-dihydro-5H-benzo[b]carbazole-3-carbonitrile hydrochloride is between 0.2 μm and 20 μm.

28. The pharmaceutical composition according to claim 26, wherein the particle size of the micronized 9-ethyl-6,6-dimethyl-8-(4-morpholin-4-yl-piperidin-1-yl)-1 1-oxo-6,1 1-dihydro-5H-benzo[b]carbazole-3-carbonitrile hydrochloride is between 0.2 μm and 15 μm.

29. The pharmaceutical composition according to claim 26, wherein the particle size of the micronized 9-ethyl-6,6-dimethyl-8-(4-morpholin-4-yl-piperidin-1-yl)-1 1-oxo-6,1 1-dihydro-5H-benzo[b]carbazole-3-carbonitrile hydrochloride is between 0.2 μm and 8 μm.

30. The pharmaceutical composition according to claim 21, comprising only one active ingredient or pharmaceutically acceptable salt thereof, which is 9-ethyl-6,6-dimethyl-8-(4-morpholin-4-yl-piperidin-1-yl)-1 1-oxo-6,1 1-dihydro-5H-benzo[b]carbazole-3-carbonitrile hydrochloride.

31. The pharmaceutical composition according to claim 21, comprising from 20 to 250 mg of the free base equivalent of 9-ethyl-6,6-dimethyl-8-(4-morpholin-4-yl-piperidin-1-yl)-11-oxo-6,11-dihydro-5H-benzo[b]carbazole-3-carbonitrile hydrochloride.

32. The pharmaceutical composition according to claim 21, comprising from 20 to 225 mg of the free base equivalent of 9-ethyl-6,6-dimethyl-8-(4-morpholin-4-yl-piperidin-1-yl)- 11-oxo-6, 11 -dihydro-5H-benzo[b]carbazole-3-carbonitrile hydrochloride.

33. The pharmaceutical composition according to claim 21, comprising from 100 to 200 mg of the free base equivalent of 9-ethyl-6,6-dimethyl-8-(4-morpholin-4-yl-piperidin-1-yl)-11-oxo-6,1 1-dihydro-5H-benzo[b]carbazole-3-carbonitrile hydrochloride.

34. The pharmaceutical composition according to claim 21, comprising from 125 to 175 mg of the free base equivalent of 9-ethyl-6,6-dimethyl-8-(4-morpholin-4-yl-piperidin-1-yl)-1 1-oxo-6,1 1-dihydro-5H-benzo[b]carbazole-3-carbonitrile hydrochloride.

35. The pharmaceutical composition according to claim 21, characterized in that the drop point of the pharmaceutical composition is between 35 and 39° C.

36. The pharmaceutical composition according to claim 21, wherein surfactant A is lauroyl polyoxylglyceride with a HLB of 14 and a drop point of 44° C.

37. The pharmaceutical composition according to claim 21, comprising surfactant A and B in a ratio in weight of 7:3.

38. The pharmaceutical composition according to claim 21, comprising;
20 to 225 mg of the free base equivalent of 9-ethyl-6,6-dimethyl-8-(4-morpholin-4-yl-piperidin-1-yl)-1 1-oxo-6,1 1-dihydro-5H-benzo[b]carbazole-3-carbonitrile hydrochloride,
150 to 300 mg of lauroyl polyoxylglyceride, and
50 to 150 mg of polysorbate 80.

39. The pharmaceutical composition according to claim 21, comprising:
150 mg of free base equivalent of 9-ethyl-6,6-dimethyl-8-(4-rnorpholin-4-yl-piperidin-1-yl)-11-oxo-6, 11 -dihydro-5H-benzo[b]carbazole-3-caronitrile hydrochloride,
245 mg of lauroyl polyoxylglyceride, and
105 mg of polysorbate 80.

40. The pharmaceutical composition according to claim 21, comprising:
- 161 mg of 9-ethyl-6,6-dimethyl-8-(4-morpholin-4-yl-piperidin-1-yl)-11-oxo-6,11-dihydro-5H-benzo[b]carbazole-3-carbonitrile hydrochloride,
- 245 mg of lauroyl polyoxylglyceride, and
- 105 mg of polysorbate 80.

41. A pharmaceutical composition comprising:
a) 9-ethyl-6,6-dimethyl-8-(4-morpholin-4-yl-piperidin-1-yl)-11-oxo-6,11-dihydro-5H-benzo[b]carbazole-3-carbonitrile hydrochloride,
b) a non-ionic surfactant A that is a solid at room temperature that is lauroyl polyoxylglyceride, and
c) a non-ionic surfactant B that is liquid at room temperature that is polysorbate 80,
wherein the HLB of surfactants A and B are independently equal or greater than 8,
wherein 9-ethyl-6,6-dimethyl-8-(4-morpholin-4-yl-piperidin-1-yl)-11-oxo-6,11-dihydro-5H-benxo[b]carbazole-3-carbonitrile hydrochloride is dispersed in the matrix formed by surfactants A and B, and
wherein the pharmaceutical composition is obtainable by:
a) melting surfactant A,
b) mixing melted surfactant A and liquid surfactant B, and
c) suspending 9-ethyl-6,6-dimethyl-8-(4-morpholin-4-yl-piperidin-1-yl)-11-oxo-6,11-dihydro-5H-benzo[b]carbazole-3-carbonitrile hydrochloride in the obtained mixture.

\* \* \* \* \*